United States Patent
McAnally et al.

(10) Patent No.: US 9,395,236 B2
(45) Date of Patent: Jul. 19, 2016

(54) VIBRATORY METER AND METHOD FOR DETERMINING RESONANT FREQUENCY

(75) Inventors: Craig B McAnally, Thornton, CO (US); Andrew S Kravitz, Erie, CO (US)

(73) Assignee: Micro Motion, Inc., Boulder, CO (US)

( * ) Notice: Subject to any disclaimer, the term of this patent is extended or adjusted under 35 U.S.C. 154(b) by 329 days.

(21) Appl. No.: 14/127,236

(22) PCT Filed: Jul. 13, 2011

(86) PCT No.: PCT/US2011/043861
§ 371 (c)(1),
(2), (4) Date: Dec. 18, 2013

(87) PCT Pub. No.: WO2013/009307
PCT Pub. Date: Jan. 17, 2013

(65) Prior Publication Data
US 2014/0190238 A1    Jul. 10, 2014

(51) Int. Cl.
*G01F 1/84* (2006.01)
*G01H 13/00* (2006.01)
*G01N 9/00* (2006.01)

(52) U.S. Cl.
CPC .............. *G01H 13/00* (2013.01); *G01F 1/8431* (2013.01); *G01F 1/8436* (2013.01); *G01F 1/8468* (2013.01); *G01F 1/8472* (2013.01); *G01N 9/002* (2013.01)

(58) Field of Classification Search
CPC ..................................................... G01F 1/8436
USPC ............. 73/24.01, 24.06, 30.01, 32 A, 54.01, 73/54.04, 54.05, 54.11, 54.24–54.27, 658, 73/861.351, 861.354, 861.355–861.357; 702/45–48, 100, 104–106
See application file for complete search history.

(56) References Cited

U.S. PATENT DOCUMENTS 4,420,983 A * 12/1983 Langdon .................. G01F 1/66
73/32 A
4,996,871 A *  3/1991 Romano .............. G01F 1/8431
73/32 A (Continued)

FOREIGN PATENT DOCUMENTS

EP          1306659 A2    5/2003
JP          63278586 A   11/1988

(Continued)

*Primary Examiner* — Hezron E Williams
*Assistant Examiner* — Hoang Nguyen
(74) *Attorney, Agent, or Firm* — The Ollila Law Group LLC

(57) ABSTRACT

A vibratory meter (5) is provided, including one or more flow conduits (103), one or more pickoff sensors (105, 105'), and a driver (104). Meter electronics (20) is configured to vibrate the one or more flow conduits (103) using a drive signal including an initial vibration frequency and to receive a pickoff sensor signal from the one or more pickoff sensors (105, 105') in response, iteratively offset a phase difference between the drive signal and the pickoff sensor signal by a predetermined phase increment and measure a resulting vibrational frequency and amplitude, with the offsetting operatively sweeping the vibration frequency over a predetermined vibration frequency range and therefore generating a plurality of vibration amplitudes and a corresponding plurality of vibration frequencies, and determine a substantially maximum amplitude response in the plurality of vibration amplitudes and designate the corresponding vibration frequency as comprising the resonant frequency.

20 Claims, 7 Drawing Sheets

(56) References Cited

U.S. PATENT DOCUMENTS

| | | | | |
|---|---|---|---|---|
| 5,767,665 A * | 6/1998 | Morita | ............... | G01F 1/8409 324/76.52 |
| 5,831,178 A * | 11/1998 | Yoshimura | ............ | G01F 1/8418 73/861.356 |
| 6,092,409 A * | 7/2000 | Patten | ............... | G01F 1/8413 702/100 |
| 6,347,293 B1 * | 2/2002 | Cunningham | ........ | G01F 1/8413 702/100 |
| 6,640,194 B2 * | 10/2003 | Little | ............... | H03L 7/093 324/76.52 |
| 6,950,760 B2 | 9/2005 | Henry et al. | | |
| 7,065,455 B2 * | 6/2006 | Henry | ............... | G01F 1/8486 702/56 |
| 7,065,465 B2 | 6/2006 | Henry et al. | | |
| 7,421,350 B2 * | 9/2008 | Duffill | ............... | G01F 1/8413 702/45 |
| 7,441,469 B2 * | 10/2008 | Shelley | ............... | G01F 1/8436 702/45 |
| 7,716,995 B2 * | 5/2010 | Patten | ............... | G01F 1/8413 73/861.355 |
| 2001/0039841 A1 * | 11/2001 | Van Cleve | ............ | G01F 1/8409 73/861.357 |
| 2004/0064271 A1 * | 4/2004 | Hays | ............... | G01F 1/8477 702/45 |
| 2007/0131024 A1 * | 6/2007 | Drahm | ............... | G01F 1/8413 73/54.27 |
| 2008/0281535 A1 * | 11/2008 | Rensing | ............... | G01F 1/8413 702/56 |
| 2010/0299089 A1 * | 11/2010 | Stack | ............... | G01F 1/74 702/48 |
| 2013/0055827 A1 * | 3/2013 | Bierweiler | ............... | G01F 1/74 73/861.355 |
| 2014/0116156 A1 * | 5/2014 | Henry | ............... | G01F 1/8404 73/861.356 |

FOREIGN PATENT DOCUMENTS

| | | |
|---|---|---|
| KR | 1020070114837 A | 12/2007 |
| WO | 2006104485 A1 | 10/2006 |
| WO | 2007035376 A2 | 3/2007 |

* cited by examiner

VIBRATORY METER AND METHOD FOR DETERMINING RESONANT FREQUENCY

BACKGROUND OF THE INVENTION

1. Field of the Invention

The present invention relates to a vibratory meter and method, and more particularly, to a vibratory meter and method for determining a resonant frequency.

2. Statement of the Problem

Vibrating conduit sensors, such as Coriolis mass flowmeters and vibrating densitometers, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness, and damping characteristics of the conduit and the material therein.

A typical Coriolis mass flowmeter includes one or more conduits that are connected inline in a pipeline or other transport system and convey material, e.g., fluids, slurries, emulsions, and the like, in the system. Each conduit may be viewed as having a set of natural vibration modes, including for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation. The instrumentation receives signals from the two pickoff sensors and processes the signals in order to derive a mass flow rate measurement, among other things.

Vibratory meters, such as Coriolis mass flow meters and vibratory densitometers, may locate and measure a resonant frequency of a vibrating flow conduit or conduits. The resonant frequency can comprise a resonant frequency of the empty flow conduit or conduits or can comprise a resonant frequency of a fluid-filled vibratory meter. The flow material can be flowing or stationary. The measured vibrational frequency of the empty flow conduit(s) may be taken into account when processing the measured resonant frequency of the fluid-filled vibratory meter, in order to obtain the density of the fluid alone.

The resonant frequency may be used to determine the density ($\rho$) of the flow material. The density may be determined from $\rho = C(1/f)^2$, where f is the measured resonant frequency and C is a calibration constant. In addition, the resonant frequency may be used in determining a mass flow rate of the flow material and may be useful in generating other fluid characteristics.

The flow material can comprise any manner of fluid, including liquids, gases, or mixtures of liquids, gases, and/or solids. Because gases have much lower densities than liquids, any error in measured resonant frequency will affect gas density measurements far more than an error will affect liquid density measurements. In addition, a small frequency error may translate into a much larger gas density error than for a liquid density measurement.

ASPECTS OF THE INVENTION

In one aspect of the invention, a vibratory meter comprises:
one or more flow conduits;
one or more pickoff sensors affixed to the one or more flow conduits;
a driver configured to vibrate the one or more flow conduits; and
meter electronics coupled to the one or more pickoff sensors and to the driver, with the meter electronics being configured to vibrate the one or more flow conduits of the vibratory meter using a drive signal including an initial vibration frequency and to receive a pickoff sensor signal from the one or more pickoff sensors in response, iteratively offset a phase difference between the drive signal and the pickoff sensor signal by a predetermined phase increment and measure a resulting vibrational frequency and amplitude, with the offsetting operatively sweeping the vibration frequency over a predetermined vibration frequency range and therefore generating a plurality of vibration amplitudes and a corresponding plurality of vibration frequencies, and determine a substantially maximum amplitude response in the plurality of vibration amplitudes and designate the corresponding vibration frequency as comprising the resonant frequency.

Preferably, the meter electronics is further configured to measure the resulting vibrational frequency and the resulting vibrational amplitude after a predetermined settling period from the offsetting.

Preferably, the drive signal includes a substantially constant amplitude.

Preferably, the vibratory meter comprises a vibrating densitometer, a vibrating gas densitometer, or a Coriolis mass flow meter.

Preferably, the meter electronics is further configured to use the resonant frequency to generate one or more flow material quantifications.

Preferably, the predetermined vibration frequency range is selected to include a presumed resonant frequency.

Preferably, the meter electronics is further configured to narrow the predetermined vibration frequency range to a predetermined narrowed frequency range after the resonant frequency is found, and the offsetting and determining is repeated in order to locate the resonant frequency within the predetermined narrowed frequency range.

Preferably, the meter electronics is further configured to narrow the predetermined vibration frequency range to a predetermined narrowed frequency range after the resonant frequency is found, with the predetermined narrowed frequency range being substantially centered on the found resonant frequency and the offsetting and determining is repeated in order to locate the resonant frequency within the predetermined narrowed frequency range.

Preferably, the meter electronics is further configured to widen the predetermined vibration frequency range to a predetermined widened frequency range if the resonant frequency is not found, and wherein the offsetting and determining is repeated in order to locate the resonant frequency within the predetermined widened frequency range.

Preferably, the resonant frequency can be determined for one or both of a particular vibratory meter or a particular flow material.

In one aspect of the invention, a method of determining resonant frequency in a vibratory meter comprises:

vibrating one or more flow conduits of the vibratory meter using a drive signal including an initial vibration frequency and receiving a pickoff sensor signal in response;

iteratively offsetting a phase difference between the drive signal and the pickoff sensor signal by a predetermined phase increment and measuring a resulting vibrational frequency and amplitude, with the offsetting operatively sweeping the vibration frequency over a predetermined vibration frequency range and therefore generating a plurality of vibration amplitudes and a corresponding plurality of vibration frequencies; and determining a substantially maximum amplitude response in the plurality of vibration amplitudes and designating the corresponding vibration frequency as comprising the resonant frequency.

Preferably, the method further comprises measuring the resulting vibrational frequency and the resulting vibrational amplitude after a predetermined settling period from the offsetting.

Preferably, the drive signal includes a substantially constant amplitude.

Preferably, the vibratory meter comprises a vibrating densitometer, a vibrating gas densitometer, or a Coriolis mass flow meter.

Preferably, the method further comprises using the resonant frequency to generate one or more flow material quantifications.

Preferably, the predetermined vibration frequency range is selected to include a presumed resonant frequency.

Preferably, the predetermined vibration frequency range is narrowed to a predetermined narrowed frequency range after the resonant frequency is found, wherein the offsetting and determining is repeated in order to locate the resonant frequency within the predetermined narrowed frequency range.

Preferably, the predetermined vibration frequency range is narrowed to a predetermined narrowed frequency range after the resonant frequency is found, with the predetermined narrowed frequency range being substantially centered on the found resonant frequency and the offsetting and determining is repeated in order to locate the resonant frequency within the predetermined narrowed frequency range.

Preferably, the predetermined vibration frequency range is widened to a predetermined widened frequency range if the resonant frequency is not found, and wherein the offsetting and determining is repeated in order to locate the resonant frequency within the predetermined widened frequency range.

Preferably, the resonant frequency can be determined for one or both of a particular vibratory meter or a particular flow material.

DETAILED DESCRIPTION OF THE INVENTION

FIGS. 1-8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
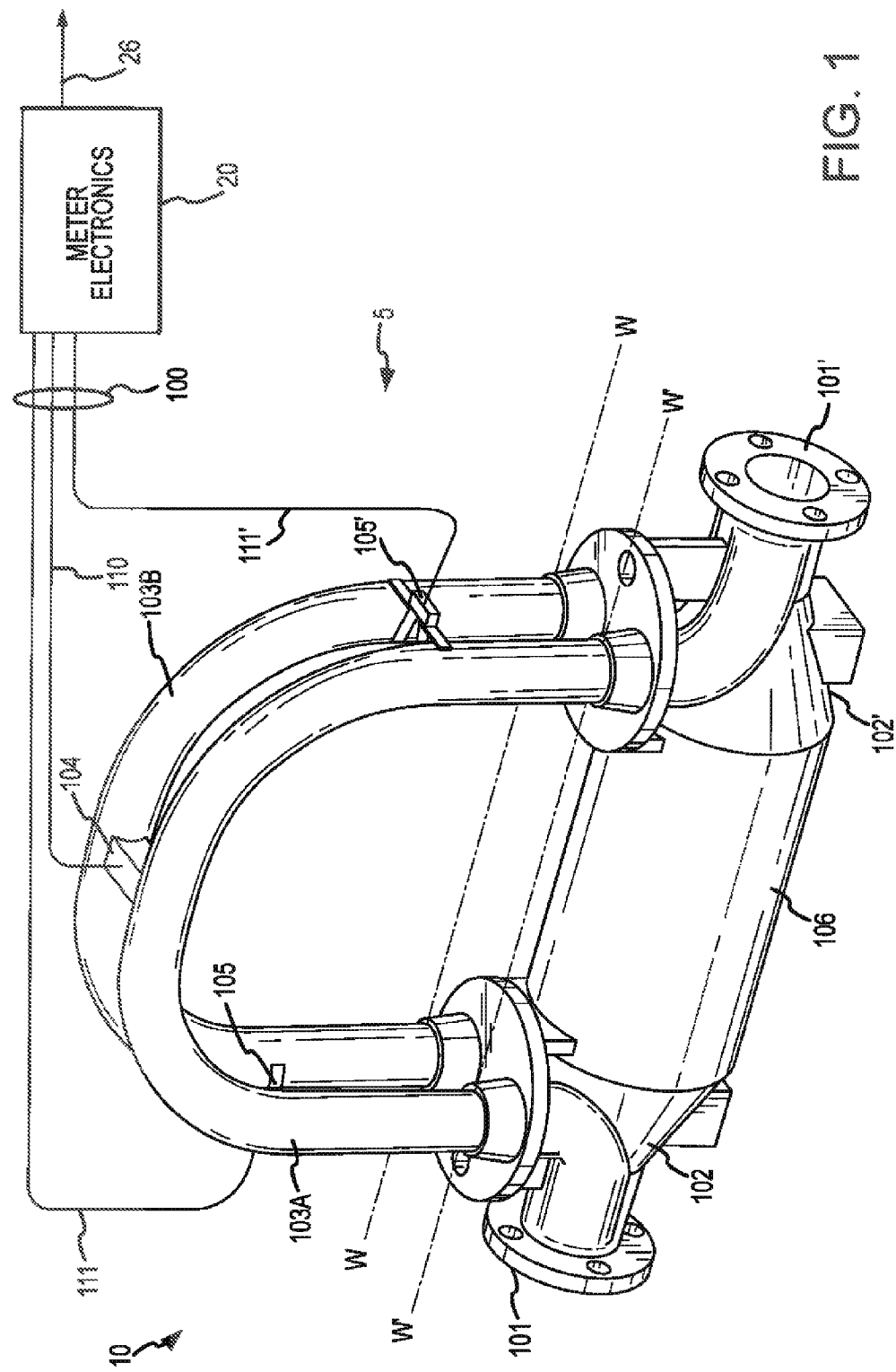
FIG. 1 shows a vibratory meter comprising a vibratory meter assembly and meter electronics according to an embodiment of the invention.

FIG. 1 shows a vibratory meter 5 comprising a vibratory meter assembly 10 and meter electronics 20 according to an embodiment of the invention. The vibratory meter 5 can comprise a Coriolis mass flow meter, and can also operate as a vibratory densitometer 5. Meter electronics 20 is connected to meter assembly 10 via leads 100 to provide density, mass flow rate, volume flow rate, totalized mass flow, temperature, and other information over path 26.

Vibratory meter assembly 10 includes a pair of flanges 101 and 101', manifolds 102 and 102', driver 104, pick-off sensors 105-105', and flow conduits 103A and 103B. Driver 104 and pick-off sensors 105 and 105' are connected to flow conduits 103A and 103B. It should be understood that the vibratory meter 5 can include flow conduits 103A, 103B of any shape, size, material, or configuration. The vibratory meter 5 can include any number of flow conduits.

Flanges 101 and 101' are affixed to manifolds 102 and 102'. Manifolds 102 and 102' are affixed to opposite ends of spacer 106. Spacer 106 maintains the spacing between manifolds 102 and 102' to prevent undesired vibrations in flow conduits 103A and 103B. When vibratory meter assembly 10 is inserted into a pipeline system (not shown) which carries the material being measured, material enters vibratory meter assembly 10 through flange 101, passes through inlet manifold 102 where the total amount of material is directed to enter flow conduits 103A and 103B, flows through flow conduits 103A and 103B and back into outlet manifold 102' where it exits meter assembly 10 through flange 101'.

Flow conduits 103A and 103B are selected and appropriately mounted to inlet manifold 102 and outlet manifold 102' so as to have substantially the same mass distribution, moments of inertia, and elastic modules about bending axes W-W and W'-W' respectively. The flow conduits extend outwardly from the manifolds in an essentially parallel fashion.

Flow conduits 103A-B are driven by driver 104 in opposite directions about their respective bending axes W and W' and at what is termed the first out-of-phase bending mode of the flow meter. Driver 104 may comprise one of many well-known arrangements, such as a magnet mounted to flow conduit 103A and an opposing coil mounted to flow conduit 103B. An alternating current is passed through the opposing coil to cause both conduits to oscillate. A suitable drive signal is applied by meter electronics 20, via lead 110 to driver 104.

Meter electronics 20 transmits sensor signals on leads 111 and 111', respectively. Meter electronics 20 produces a drive signal on lead 110 which causes driver 104 to oscillate flow conduits 103A and 103B. Meter electronics 20 processes the left and right velocity signals that are received from the pickoff sensors 105 and 105' in order to compute a mass flow rate measurement. Path 26 provides an input and an output means that allows meter electronics 20 to interface with an operator and/or other devices.

The description of FIG. 1 is provided merely as an example of the operation of a Coriolis flow meter and/or vibratory densitometer, and is not intended to limit the teaching of the present invention.

The vibratory meter 5 in some embodiments comprises a densitometer. The vibratory meter 5 in some embodiments comprises a gas densitometer. Alternatively, the vibratory meter 5 may comprise a Coriolis mass flow meter.

Figure 2:
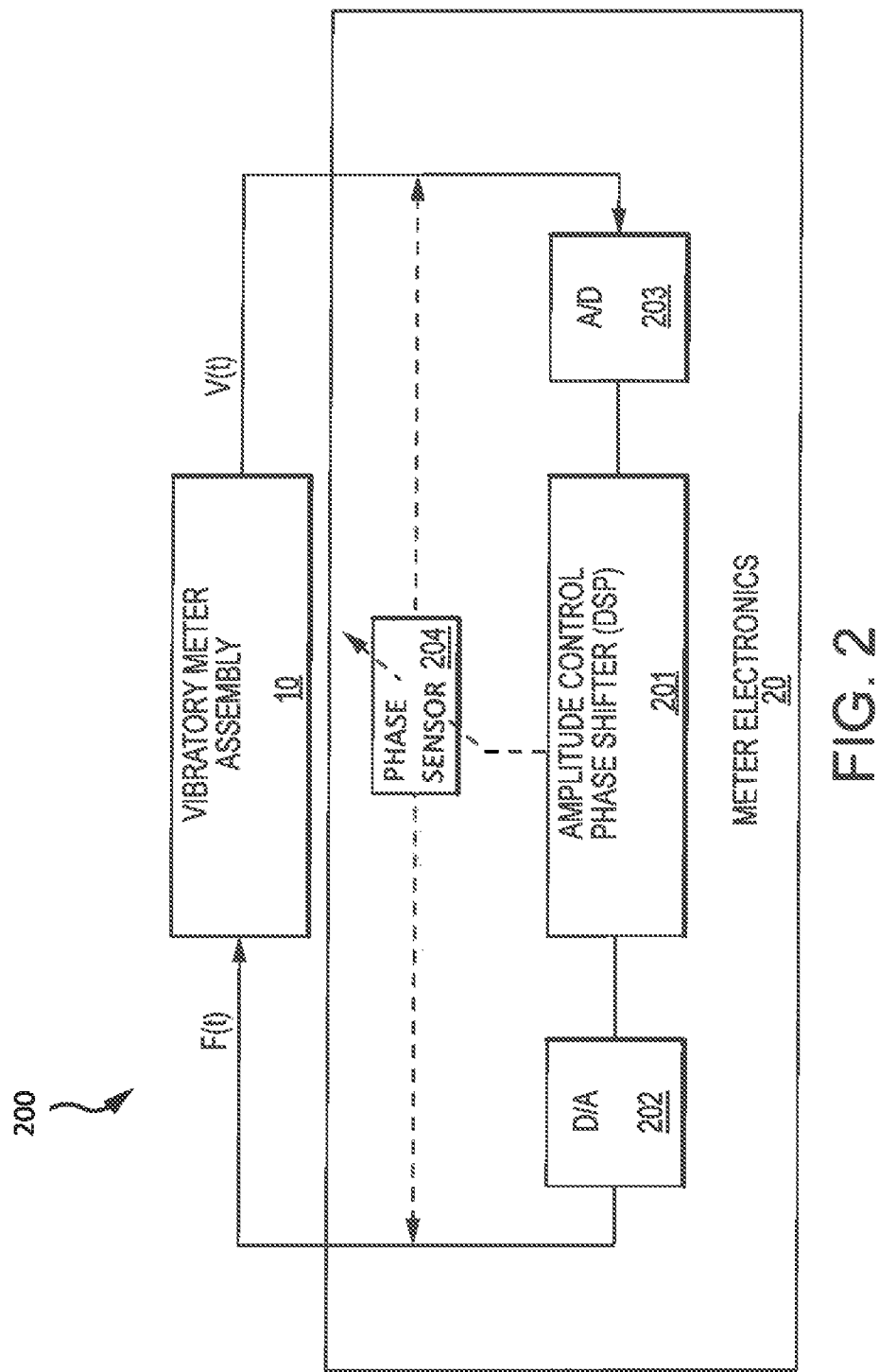
FIG. 2 shows the meter electronics coupled to the vibratory meter assembly according to an embodiment of the invention.

FIG. 2 shows the meter electronics 20 coupled to the vibratory meter assembly 10 according to an embodiment of the invention. The meter electronics 20 includes a feedback loop. The feedback loop receives a pickoff sensor signal from the vibratory meter assembly 10. The feedback loop generates a drive signal and provides the drive signal to the vibratory meter assembly 10.

The feedback loop in the embodiment shown includes a phase shifter 201, a digital-to-analog (D/A) converter 202, an analog-to-digital (A/D) converter 203, and a phase sensor 204. In operation, the phase shifter 201 generates a digital drive signal that is converted to an analog drive signal by the D/A 202 and provided to the fluid sensor 200. The pickoff signal is provided to the A/D 203, which digitizes the analog pickoff signal and provides it to the phase shifter 201. The phase sensor 204 compares the input (i.e., drive signal) phase to the output (i.e., pickoff signal) phase, and generates a phase difference signal that is provided to the phase shifter 201. As a result, the phase shifter 201 can control the phase shift and the frequency of the drive signal provided to the fluid sensor 200. Not shown is an amplifier that can adjust the amplitude of the drive signal. The drive signal amplitude is typically greater than the pickoff signal amplitude.

The meter electronics 20 therefore receives a pickoff sensor signal and generates a drive signal based at least in part on the pickoff sensor signal. The drive signal frequency can be based on or identical to the pickoff signal frequency. The drive signal amplitude can be based on or identical to the pickoff signal amplitude. The phase difference between the drive signal phase and the pickoff signal phase can also be determined and controlled by the meter electronics 20.

In addition, the meter electronics 20 can be operated to determine a resonant frequency of the vibratory meter assembly 10. The meter electronics 20 is configured to vibrate the one or more flow conduits 103 of the vibratory meter assembly 10 using a drive signal including an initial vibration frequency and receive a pickoff sensor signal from the one or more pickoff sensors 105, 105' in response, iteratively offset a phase difference between the drive signal and the pickoff sensor signal by a predetermined phase increment and measure a resulting vibrational frequency and amplitude, with the offsetting operatively sweeping the vibration frequency over a predetermined vibration frequency range and therefore generating a plurality of vibration amplitudes and a corresponding plurality of vibration frequencies, and determine a substantially maximum amplitude response in the plurality of vibration amplitudes and designate the corresponding vibration frequency as comprising the resonant frequency.

The meter electronics 20 is configured to control the phase between the input and the output of the fluid sensor 200 so as to offset the phase difference and therefore change the vibration frequency. The vibration frequency will be made to change by the phase difference offset, although the frequency may not immediately track the phase offset. The meter electronics 20 in some embodiments will wait for a settling period after the phase offsetting before measuring the resultant vibration frequency. For example, in some embodiments, the predetermined settling period may be about 50 milliseconds. However, other settling periods are contemplated and are within the scope of the description and claims.

The meter electronics 20 is configured to iteratively offset the phase difference so as to sweep the vibration frequency over the predetermined vibration frequency range while maintaining the system under closed-loop control. Such phase control can be digitally implemented using standard phase-locked loop techniques. In one embodiment, the closed-loop control can be performed by an appropriately programmed Digital Signal Processor (DSP). However, other feedback or loop control techniques can be employed and are within the scope of the description and claims.

The apparatus and method accurately determine the resonant frequency. As the density of the gas or liquid changes, the resonant frequency of the sensor changes. The determined resonant frequency can be used to generate an accurate density measurement. In addition, the determined resonant frequency may also be used to generate an optimal drive frequency.

The apparatus and method find special utility in vibratory gas densitometers where variations in gas density are relatively small. An accurate determination of resonant frequency is of great importance in vibratory densitometers. Consequently, any errors in resonant frequency determination for a gas may have a relatively large impact on density measurement accuracy. The apparatus and method may also be used in liquid or multi-phase densitometers. Gas densitometers may differ from liquid densitometers by being constructed to have a lower flexural stiffness and a higher vibrational frequency. However, an accurate frequency and/or density is also desirable in liquid or multi-phase densitometers. The determined resonant frequency can also be used in Coriolis mass flow meters, although locating the actual resonant frequency for a mass flow measurement may not be as critical as for density measurements.

The determined resonant frequency can be used to derive flow material quantifications. The determined resonant frequency can be used to determine a flow material density. The determined resonant frequency can be used to determine a flow material mass flow rate. Other flow material quantifications include void fraction, liquid fraction, mass fraction, viscosity, and/or volume flow rate. Additional flow material quantifications are contemplated and are within the scope of the description and claims.

Figure 3:
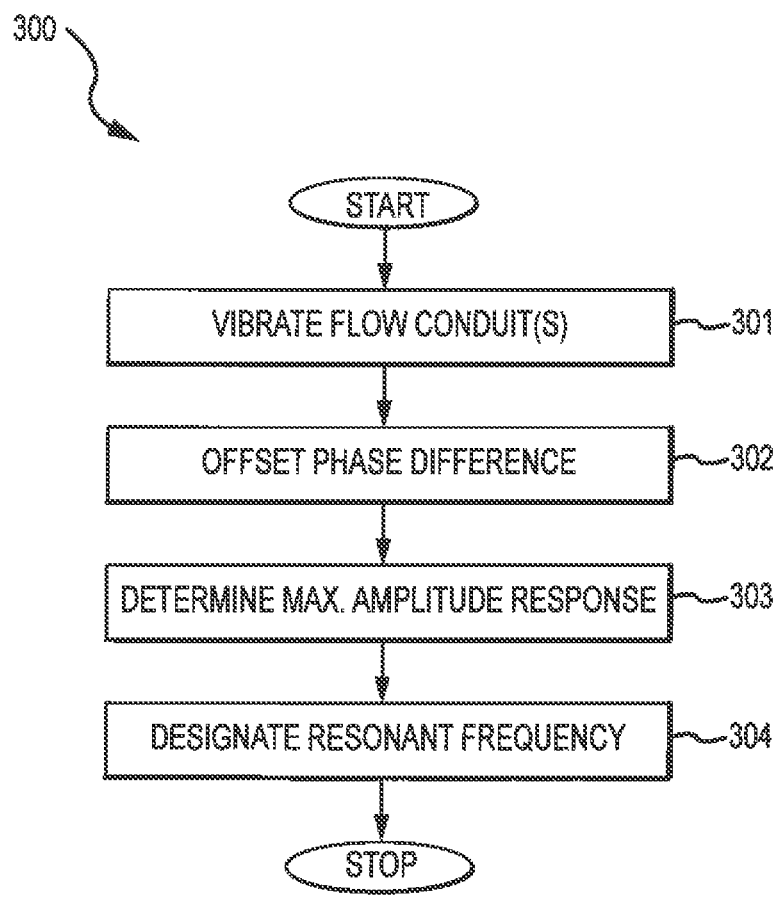
FIG. 3 is a flowchart of a method of determining resonant frequency in a vibratory meter according to an embodiment of the invention.

FIG. 3 is a flowchart 300 of a method of determining resonant frequency in a vibratory meter according to an embodiment of the invention. In step 301, the one or more flow conduits 105, 105' of the vibratory meter 5 are vibrated using the driver 104 and a drive signal. The drive signal includes a vibration frequency. At a beginning of a resonant frequency search, the vibration frequency comprises an initial vibration frequency. The drive signal also includes a vibration amplitude. In some embodiments, the vibration amplitude is held at a substantially constant level. As a result, the vibration signal may specify a substantially constant vibration power.

The meter electronics 20 generates the drive signal using a pickoff sensor signal from one of the pickoff sensor signals. Only one pickoff sensor signal is needed in order to generate the drive signal. In addition, only one pickoff sensor signal is needed in order to determine the resonant frequency. The pickoff sensor signal from either pickoff sensor 105 or 105' may be used in the resonant frequency determination.

The pickoff sensor signal will be related to the drive signal in frequency, phase, and amplitude. However, the pickoff sensor signal will not necessarily be identical to the drive signal. The pickoff sensor signal will have a lesser amplitude than the drive signal, as some amplitude loss will occur. The pickoff sensor signal may have a different frequency, as the one or more flow conduits 105, 105' may vibrate at one or more resultant frequencies that may differ from the drive frequency, especially where the resonant frequency is assumed and not found. Lastly, the pickoff sensor signal may lag the drive signal in phase, such as in normal operation and/or where the drive signal frequency remains essentially constant over time.

In step 302, the phase difference is offset by a predetermined phase increment. The phase difference comprises the difference between the drive signal phase and the pickoff sensor signal phase. The predetermined phase increment may be constant in size or may be graduated or changing, as desired. In some instances, the phase difference is offset from a substantially zero phase difference. Alternatively, the phase offset may be added to an existing phase difference.

The vibration frequency is not directly changed by the phase offsetting. However, the vibration frequency will change as a result of the phase difference offset. A predetermined settling period may need to elapse in order to ensure that the vibration frequency has changed as a result of the phase offset. As a result of iteratively offsetting the phase difference, the vibration frequency is (iteratively) swept over a predetermined vibration frequency range.

The predetermined vibration frequency range may comprise a range of frequencies that is presumed to include the resonant frequency. However, the actual density of a gas may vary according to environmental conditions, including due to temperature and pressure, for example. The expected variation of the resonant frequency may be small for a gas, such as less than one Hertz, for example. The gas density may change slowly or may change substantially instantaneously. As a result, the resonant frequency of a gas-filled vibratory meter may change over time. The resonant frequency variation will correlate to a density variation, wherein the density ($\rho$) comprises $\rho = C_{density}(1/f)^2$. The $C_{density}$ term may comprise a calibration constant.

In the prior art, the frequency was swept in order to detect a maximum amplitude response and subsequently find the resonant frequency. In the prior art, the phase difference was considered to be essentially fixed and was not accounted for in determining the resonant frequency. Unfortunately, the variations in phase difference, and a lack of compensation for any phase difference, resulted in the prior art finding a resonant frequency that could be inaccurate.

In step 303, as the phase difference is offset in order to sweep the vibration frequency through the predetermined vibration frequency range, the resulting amplitude of the pickoff sensor signal is monitored. A substantially maximum amplitude response is determined. In addition, a corresponding vibration frequency is determined. Here, the maximum amplitude response of the pickoff sensor signal will be seen when the vibration frequency is at substantially the resonant frequency.

As previously discussed, in some embodiments the method will wait for a settling period after the phase offsetting before measuring the resultant vibration frequency. For example, in some embodiments, the predetermined settling period may be about 50 milliseconds. However, other settling periods are contemplated and are within the scope of the description and claims.

In step 304, the resonant frequency is determined. The phase difference offsetting is used to increase or decrease the vibration frequency and generate a plurality of vibration frequencies and a corresponding plurality of vibration amplitudes. A maximum amplitude response substantially corresponds to the resonant frequency, as previously discussed. The resonant frequency is determined as comprising the vibration frequency among the plurality of vibration frequencies that produces the maximum amplitude response. Alternatively, the resonant frequency may be designated where the designated vibration frequency is closest to the maximum amplitude response, where the resonant frequency occurs between two adjacent vibration frequencies.

The accuracy of the determined resonant frequency can be controlled by choosing the size of the predetermined phase increment. The size of the predetermined phase increment can be chosen in order to achieve a desired frequency resolution and a desired accuracy. A smaller phase increment will produce a more accurate resonant frequency, at a finer frequency resolution, but may require more iterations and therefore more search time. But the resolution can be very fine, if desired, such as the capability of resolving resonant frequency on the scale of a few milliHertz (mHz) in some embodiments.

The determined resonant frequency can be used to derive one or more flow material quantifications, as previously discussed. The determined resonant frequency can be determined for a particular vibratory meter. The determined resonant frequency can be found for a vibratory meter at any time, such as during normal operation. Alternatively, the determined resonant frequency can be found as part of a meter calibration or validation operation, for example. The determined resonant frequency can be determined for a particular flow material. For example, the determined resonant frequency may be obtained when a new flow material is first being metered. Alternatively, the determined resonant frequency can be found for both a particular vibratory meter and a particular flow material.

Figure 4:
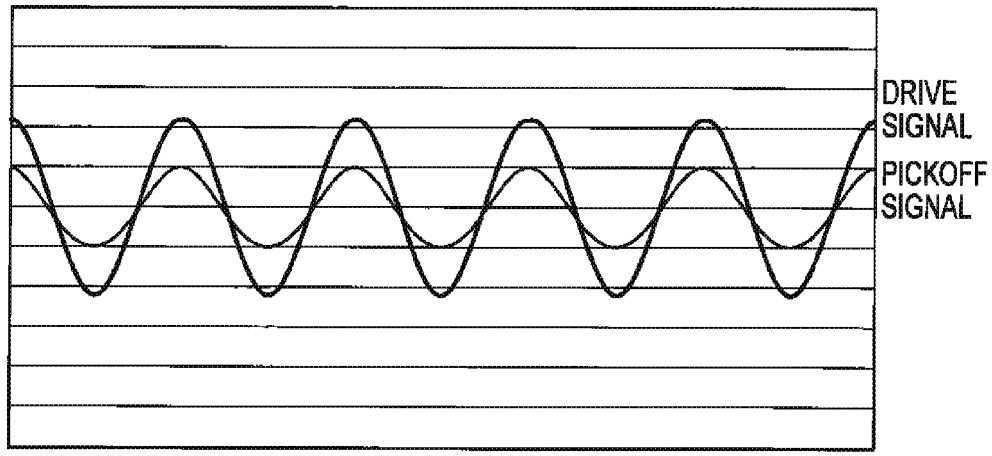
FIG. 4 is a plot of a drive signal versus a resulting pickoff signal in normal operation of the vibratory meter.

FIG. 4 is a plot of a drive signal versus a resulting pickoff signal in normal operation of the vibratory meter 5. The plot reflects a typical vibrational operation wherein the vibratory meter 5 is operating under essentially steady-state conditions. As a result, the drive signal and the pickoff signal are substantially in phase. The amplitude of the drive signal typically exceeds the amplitude of the pickoff signal, as shown, such as where energy is being added to the system to maintain the steady-state vibration.

Ideally, the phase of the drive signal will be exactly in-phase with the pick-off input signal (or 180 degrees out of phase, depending on orientation). However, all closed loop systems will have some source of potential phase shift, and therefore it is possible to drive slightly off resonance in operation.

The problem with traditional closed loop systems in this type of application is that the phase difference between the pick-off signal and the drive signal will influence the actual vibration frequency of the meter. Since the frequency of the vibratory meter assembly 10 is proportional to the density, any inaccuracy in the determined frequency, such as a phase difference, can cause frequency measurement errors.

Figure 5:
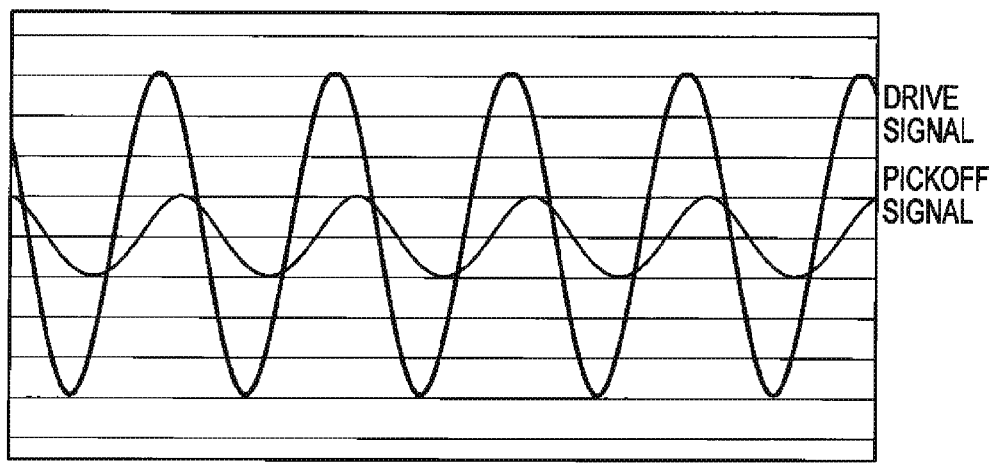
FIG. 5 is a plot of the drive signal versus pickoff signal where the pickoff signal is no longer in phase with the drive signal.

FIG. 5 is a plot of the drive signal versus pickoff signal where the pickoff signal is no longer in phase with the drive signal. If the signals are not in phase, two issues arise. First, more drive power will be required to achieve the same pickoff amplitude. This is shown in the figure, where the drive signal now has a much greater amplitude than the pickoff signal. Unfortunately, increasing the drive power reduces the maximum power overhead available in the drive, reduces the efficiency of the drive, and ultimately reduces the performance of the vibratory meter 5.

The second issue is that by not driving in phase, the actual frequency being measured is not the resonant frequency. Further, changes in the operating environment (such as changes in temperature, for example), the aging of the vibratory meter assembly 10, and/or damage to components, will increase this error over time. Consequently, there is a need to be able to determine the resonant frequency. There is a need to be able to determine the resonant frequency at various points in time, such as over the lifetime of the vibratory meter 5. There is a need to accurately determine resonant frequency without any phase difference affecting the accuracy of the determined resonant frequency.

Figure 6:
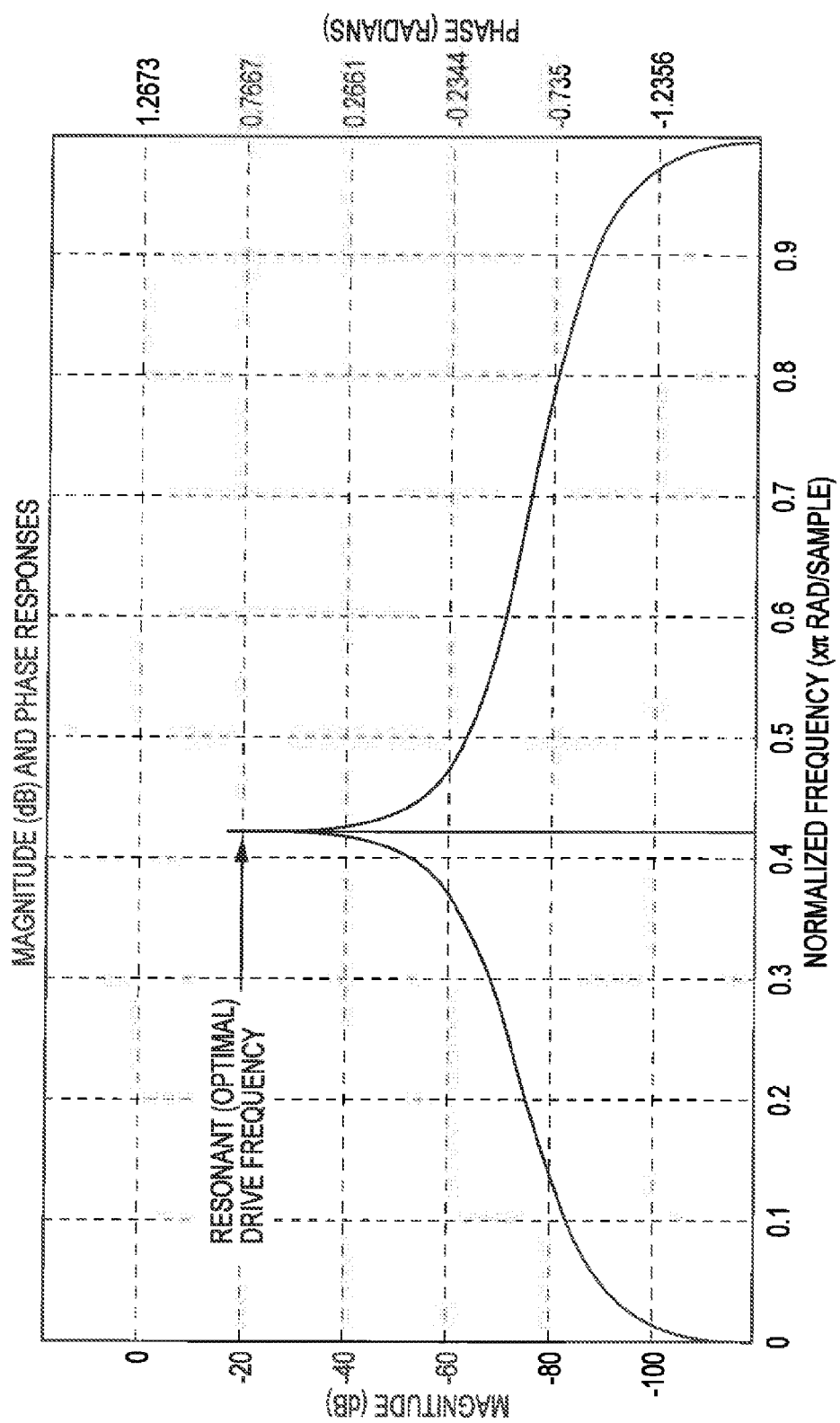
FIG. 6 is a plot of drive signal frequency (bottom axis) versus drive-pickoff phase difference (right side axis) versus pickoff signal amplitude (left side axis) in an example of the resonant frequency determination.

FIG. 6 is a plot of drive signal frequency (bottom axis) versus drive-pickoff phase difference (right side axis) versus pickoff signal amplitude (left side axis) in an example of the resonant frequency determination. In the plot, the drive power has been held constant while the phase of the drive signal relative to the pickoff signal has been iteratively offset. A typical phase increment may be in a range of about (−1.2356) to (+1.2673) degrees of phase offset, for example. However, other phase increments are contemplated and are within the scope of the description and claims.

The resonant frequency determination takes advantage of the resonant nature of the sensing element, i.e., the resonant response that may be generated in the vibratory meter assembly 10. The sensor will exhibit a very sharp amplitude peak at the resonant frequency. By offsetting the phase of the drive signal relative to the phase of the pickoff signal, it is possible to move the vibration frequency up and down the frequency spectrum. Here, it can be seen that the pickoff signal magnitude will show a sharp (i.e., resonant) peak as the vibration frequency is forced to change through phase difference offsetting.

Figure 7:
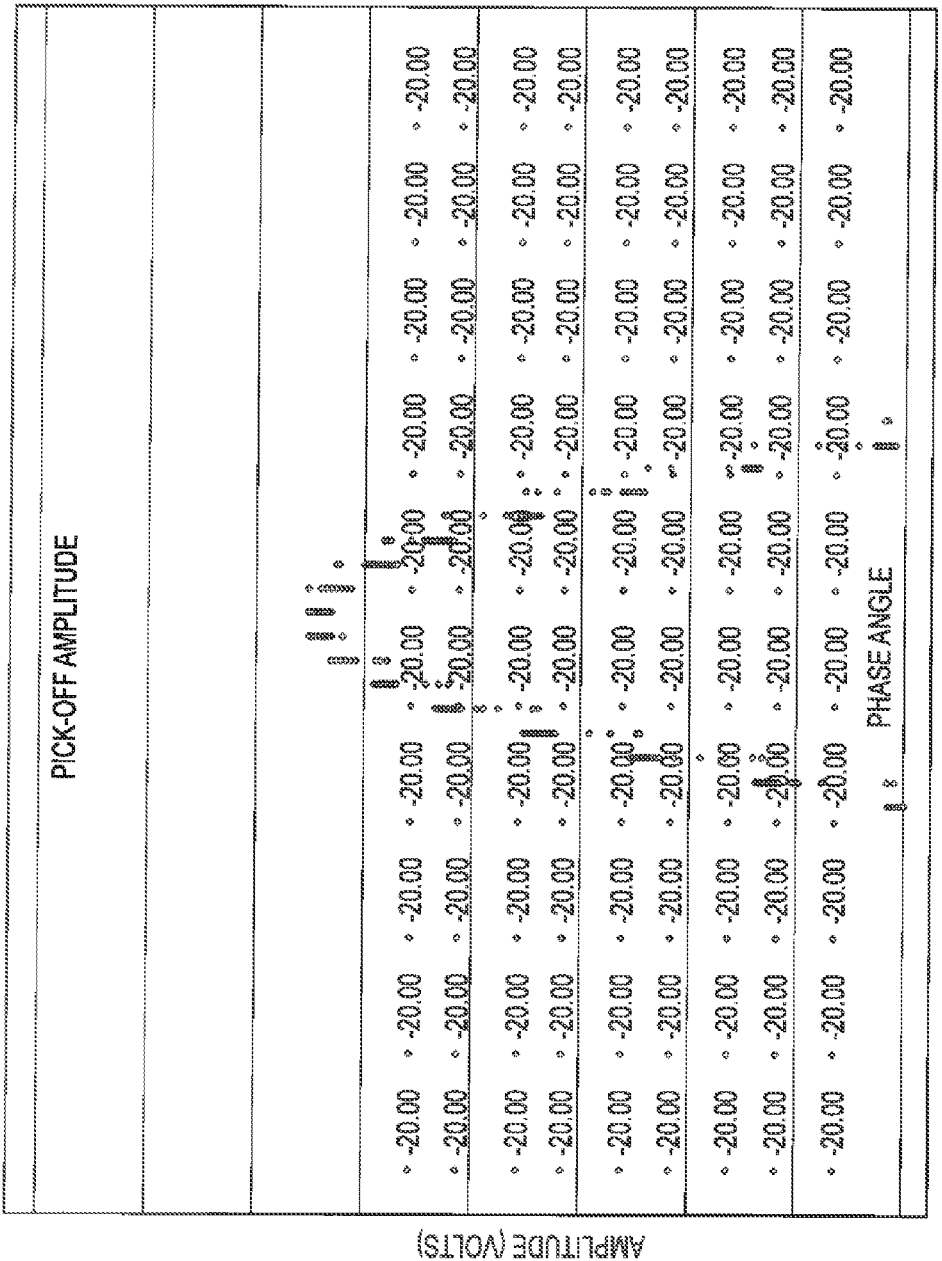
FIG. 7 shows the results of adjusting the relative phase between the pick-off signal and the drive on a gas densitometer.

FIG. 7 shows the result of offsetting the relative phase between the pick-off signal and the drive signal in a gas densitometer. When the sensor is driving on resonance, the pick-off amplitude is at its peak. By locating the peak using this algorithm, it is therefore possible to guarantee that the transmitter is producing the substantially optimal drive signal.

Figure 8:
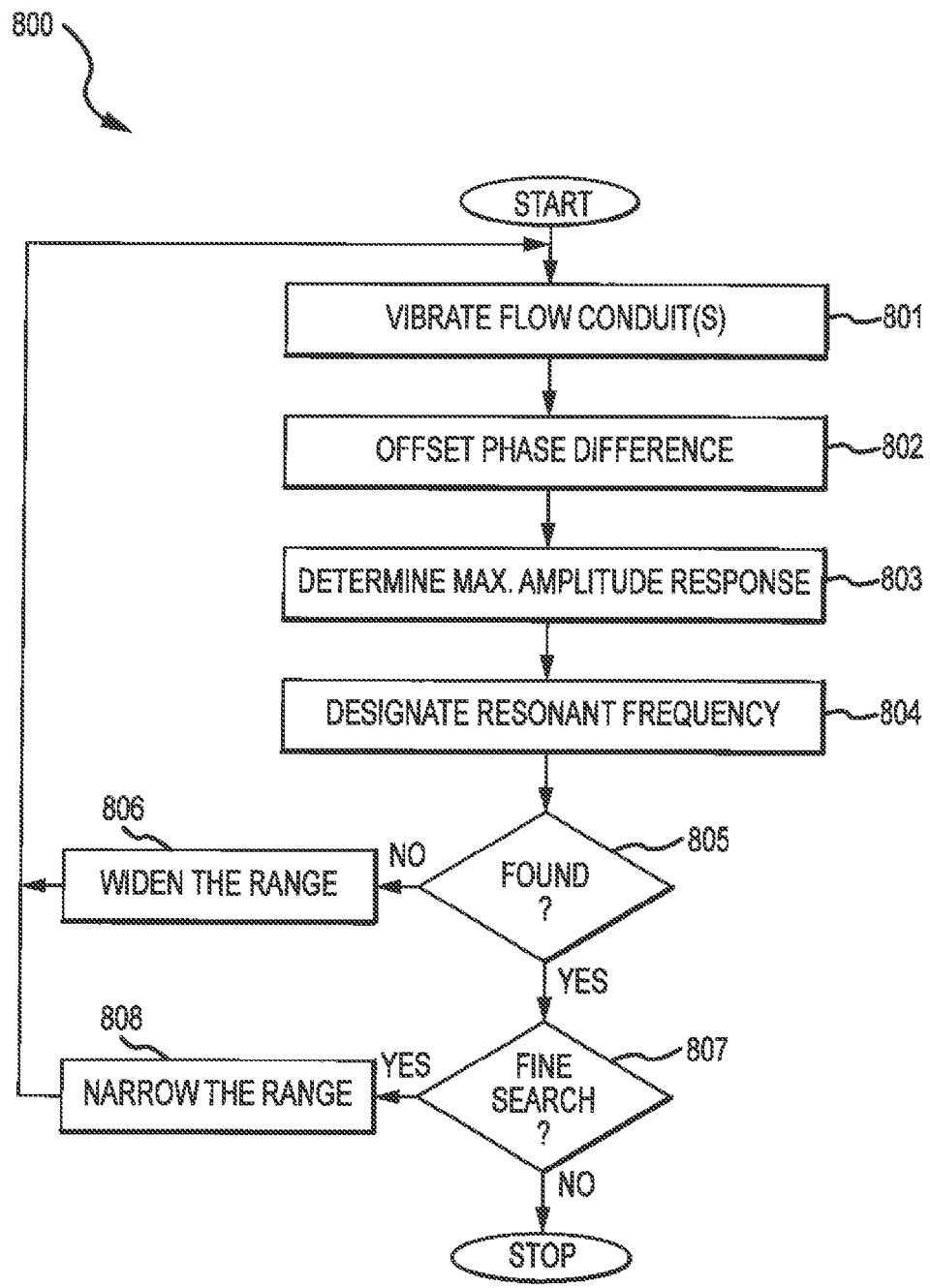
FIG. 8 is a flowchart of a method of determining resonant frequency in a vibratory meter according to an embodiment of the invention.

FIG. 8 is a flowchart 800 of a method of determining resonant frequency in a vibratory meter according to an embodiment of the invention. In step 801, the one or more flow conduits 105, 105' of the vibratory meter 5 are vibrated, as previously discussed.

In step 802, the phase difference is offset by a predetermined phase increment, as previously discussed.

In step 803, the resulting amplitude of the pickoff sensor signal is monitored, as previously discussed.

In step 804, the resonant frequency is determined, as previously discussed.

In step 805, if the resonant frequency has been found, then the method proceeds to step 807. Otherwise, where the resonant frequency has not been found, the method branches to step 806.

In step 806, the predetermined vibration frequency range is widened. The method then loops back to step 801 and the resonant frequency search is repeated, but with the wider predetermined vibration frequency range.

The predetermined vibration frequency range may be widened by a predetermined amount. For example, the predetermined vibration frequency range could be increased by fifty percent, could be doubled, or could be widened in other ways and by other amounts. As a result, the frequency sweep will cover a larger range of frequencies. This may be done in order to start with a narrow, relatively fine search resolution, wherein a wide, coarse resolution resonant frequency search is only performed if the narrow resonant frequency search fails.

The predetermined phase increment may be kept the same. Alternatively, for a wide, coarse resolution resonant frequency search, the predetermined phase increment may be made larger, in keeping with the wider predetermined vibration frequency range, or may be made smaller in order to produce a finer frequency resolution even as a wider predetermined vibration frequency range is being searched.

In step 807, if a fine search is needed, the method branches to step 808. Otherwise, where a narrower, fine resonant frequency search is not needed, the method exits.

The decision may be an automatic decision, wherein a coarse search is performed, and then a fine search is performed, with a new, narrow predetermined vibration frequency range being used for the fine search. The new, narrow predetermined vibration frequency range may be centered on or may include the determined resonant frequency found in step 804.

Alternatively, the need for a fine search may be based on an imputed resonant frequency. It may be determined from the produced vibration frequencies that the maximum vibration amplitude does not occur at, or within a predetermined threshold of, the vibration frequency that produced the maximum vibration amplitude. For example, two identical strongest amplitude values may be produced at two adjacent frequencies, wherein the actual amplitude response peak will reside somewhere between the two vibration frequencies. However, if the actual peak is within a predetermined threshold, the method may judge that a fine search is not needed.

It should be understood that the method of determining resonant frequency may include both the widening process and the narrowing process, as shown in the flowchart. Alternatively, the method may include just the widening process for performing a coarser search. In yet another alternative, the method may include just the narrowing process for performing a finer search.

The vibratory meter and method according to the invention can be employed according to any of the embodiments in order to provide several advantages, if desired. The vibratory meter and method may provide a more accurate resonant frequency determination than by varying the vibration frequency, as varying the vibration frequency may result in a phase difference variation that skews the frequency determination.

The vibratory meter and method may require less power by driving in phase with the pickoff signal. The vibratory meter and method may provide an improved resonant frequency detection by driving the one or more flow conduits at a substantially constant power. By driving the one or more flow conduits at a substantially constant power, an increased amplitude in a pickoff sensor signal cannot be due to an increase in vibrational power.

The vibratory meter and method may provide an improved resonant frequency detection by not varying frequency and phase at the same time. Because the pickoff sensor signal phase may differ from the drive signal phase during a frequency sweep, it is more accurate and reliable to vary only the phase difference while holding the vibration frequency constant.

The vibratory meter and method may provide an improved resonant frequency detection in densitometers. The vibratory meter and method may provide an improved resonant frequency detection in gas densitometers, where the measured density is low and small inaccuracies have a greater impact.

The vibratory meter and method may provide an improved resonant frequency detection wherein the resonant frequency can be determined for a particular vibratory meter. The vibratory meter and method may provide an improved resonant frequency detection wherein the resonant frequency can be determined for a particular flow material.

The vibratory meter and method enable periodic checking of a resonant frequency. The vibratory meter and method enable comparison of resonant frequencies over time in order to assess the condition of the subject vibratory meter.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. A vibratory meter (5) comprising one or more flow conduits (103), one or more pickoff sensors (105, 105') affixed to the one or more flow conduits (103), and a driver (104) configured to vibrate the one or more flow conduits (103), with the vibratory meter (5) being characterized by:
   meter electronics (20) coupled to the one or more pickoff sensors (105, 105') and to the driver (104), with the meter electronics (20) being configured to vibrate the one or more flow conduits (103) of the vibratory meter (5) using a drive signal including an initial vibration frequency and to receive a pickoff sensor signal from the one or more pickoff sensors (105, 105') in response, iteratively offset a phase difference between the drive signal and the pickoff sensor signal by a predetermined phase increment and measure a resulting vibrational frequency and amplitude, with the offsetting operatively resulting vibration frequency being used to sweep over a predetermined vibration frequency range and therefore generating a plurality of vibration amplitudes and a corresponding plurality of vibration frequencies, and determine a substantially maximum amplitude response in the plurality of vibration amplitudes and designate the corresponding vibration frequency as comprising a resonant frequency.

2. The vibratory meter (5) of claim 1, with the meter electronics (20) being further configured to measure the resulting vibrational frequency and the resulting vibrational amplitude after a predetermined settling period from the offsetting.

3. The vibratory meter (5) of claim 1, with the drive signal including a substantially constant amplitude.

4. The vibratory meter (5) of claim 1, with the vibratory meter (5) comprising a vibrating densitometer, a vibrating gas densitometer, or a Coriolis mass flow meter.

5. The vibratory meter (5) of claim 1, with the meter electronics (20) being further configured to use the resonant frequency to generate one or more flow material quantifications.

6. The vibratory meter (5) of claim 1, wherein the predetermined vibration frequency range is selected to include a presumed resonant frequency.

7. The vibratory meter (5) of claim 1, with the meter electronics (20) being further configured to narrow the predetermined vibration frequency range to a predetermined narrowed frequency range after the resonant frequency is found, wherein the offsetting and determining is repeated in order to locate the resonant frequency within the predetermined narrowed frequency range.

8. The vibratory meter (5) of claim 1, with the meter electronics (20) being further configured to narrow the predetermined vibration frequency range to a predetermined narrowed frequency range after the resonant frequency is found, with the predetermined narrowed frequency range being substantially centered on the found resonant frequency and the offsetting and determining is repeated in order to locate the resonant frequency within the predetermined narrowed frequency range.

9. The vibratory meter (5) of claim 1, with the meter electronics (20) being further configured to widen the predetermined vibration frequency range to a predetermined widened frequency range if the resonant frequency is not found, wherein the offsetting and determining is repeated in order to locate the resonant frequency within the predetermined widened frequency range.

10. The vibratory meter (5) of claim 1, wherein the resonant frequency can be determined for one or both of a particular vibratory meter or a particular flow material.

11. A method of determining resonant frequency in a vibratory meter, with the method including vibrating one or more flow conduits of the vibratory meter using a drive signal including an initial vibration frequency and receiving a pickoff sensor signal in response, with the method being characterized by:
   iteratively offsetting a phase difference between the drive signal and the pickoff sensor signal by a predetermined phase increment and measuring a resulting vibrational frequency and amplitude, with the offsetting operatively resulting vibration frequency being used to sweep over a predetermined vibration frequency range and therefore generating a plurality of vibration amplitudes and a corresponding plurality of vibration frequencies; and
   determining a substantially maximum amplitude response in the plurality of vibration amplitudes and designating the corresponding vibration frequency as comprising the resonant frequency.

12. The method of claim 11, with the method further comprising measuring the resulting vibrational frequency and the resulting vibrational amplitude after a predetermined settling period from the offsetting.

13. The method of claim 11, with the drive signal including a substantially constant amplitude.

14. The method of claim 11, with the vibratory meter comprising a vibrating densitometer, a vibrating gas densitometer, or a Coriolis mass flow meter.

15. The method of claim 11, with the method further comprising using the resonant frequency to generate one or more flow material quantifications.

16. The method of claim 11, wherein the predetermined vibration frequency range is selected to include a presumed resonant frequency.

17. The method of claim 11, wherein the predetermined vibration frequency range is narrowed to a predetermined narrowed frequency range after the resonant frequency is found, wherein the offsetting and determining is repeated in order to locate the resonant frequency within the predetermined narrowed frequency range.

18. The method of claim 11, wherein the predetermined vibration frequency range is narrowed to a predetermined narrowed frequency range after the resonant frequency is found, wherein the predetermined narrowed frequency range is substantially centered on the found resonant frequency and wherein the offsetting and determining is repeated in order to locate the resonant frequency within the predetermined narrowed frequency range.

19. The method of claim 11, wherein the predetermined vibration frequency range is widened to a predetermined widened frequency range if the resonant frequency is not found, wherein the offsetting and determining is repeated in order to locate the resonant frequency within the predetermined widened frequency range.

20. The method of claim 11, wherein the resonant frequency can be determined for one or both of a particular vibratory meter or a particular flow material.

* * * * *